United States Patent [19]

Hanin

[11] Patent Number: 4,658,068

[45] Date of Patent: Apr. 14, 1987

[54] HYDROFORMYLATION OF OLEFINS

[75] Inventor: Jean A. A. Hanin, Rixensart, Belgium

[73] Assignee: Exxon Research & Engineering Co., Florham Park, N.J.

[21] Appl. No.: 803,086

[22] Filed: Nov. 27, 1985

[30] Foreign Application Priority Data

Nov. 30, 1984 [GB] United Kingdom ............... 8430223

[51] Int. Cl.$^4$ ........................................... C07C 45/50
[52] U.S. Cl. .................. 568/451; 568/492; 568/883
[58] Field of Search ............... 568/451, 883, 909, 492

[56] References Cited

U.S. PATENT DOCUMENTS

| | | | |
|---|---|---|---|
| 2,595,096 | 4/1952 | Parker | 568/909 |
| 2,671,119 | 3/1954 | Mertzweiller | 568/883 |
| 2,757,203 | 7/1954 | Hale | 568/451 |
| 2,779,794 | 1/1957 | Catterall | 568/454 |
| 2,779,796 | 1/1957 | Munger | 568/451 |
| 2,905,716 | 9/1959 | Buchner et al. | 568/451 |
| 3,092,670 | 6/1963 | Gwynn et al. | 568/451 |
| 4,048,233 | 8/1977 | Ruhrchemie | 568/909 |

FOREIGN PATENT DOCUMENTS 1411073 10/1975 United Kingdom ............... 568/451

Primary Examiner—Werren B. Lone
Attorney, Agent, or Firm—J. B. Murray, Jr.

[57] ABSTRACT

The higher alcohol yield of a hydroformylation process comprising catalytic hydroformylation of olefinic feedstock and hydrogenation of the crude product is improved by separating light materials and desired alcohols from the hydrogenated product, and then subjecting the remaining heavy materials to catalytic steam cracking at 260°–380° C. The fraction of the cracked product which is rich in alcohol/aldehyde is then separated and recycled, preferably to the hydrogenation stage.

14 Claims, No Drawings

HYDROFORMYLATION OF OLEFINS

This invention relates to the hydroformylation process, which in general terms is a process involving the preparation of oxygenated organic compounds by the reaction of carbon monoxide and hydrogen (synthesis gas) with carbon compounds containing olefinic unsaturation, and is particularly concerned with the treatment and recycling of by products of the primary oxo-reaction.

The oxo reaction is performed under hydroformylation conditions in the presence of a carbonylation catalyst or catalyst precursor such as dicobaltoctacarbonyl, and results in the formation of a compound e.g. an aldehyde which has one more carbon atom in its molecular structure than the feedstock. Subsequent hydrogenation of the primary product leads to higher alcohols which may be converted into plasticizers.

Typically in higher alcohol production the feedstock for a hydroformylation process is a commercial $C_6$–$C_{12}$ olefin fraction and the desired end product is the respective $C_7$–$C_{13}$ saturated alcohol or derived mixed product, produced by hydrogenation of the aldehyde oxonation product. By virtue of the nature of the feedstock commonly available to industry, and indeed of the catalyst and reaction parameters employed, the hydroformylation reaction inevitably yields a range of products due to the numerous secondary reactions which take place. The main products of the hydroformylation unit are aldehydes and alcohols, with side reactions in the hydroformylation, demetalling and hydrogenation sections of the process system usually producing some 5 to 20 wt % of high boiling materials such as aldols, esters, ethers and acetals. Such high boiling materials, which represent a serious yield loss to the alcohol producer, are collectively termed the Heavy Oxo Fraction (HOF), and are formed in large part by condensation, esterification and dehydration reactions.

In a conventional higher oxo alcohol process, the feedstock as described above is fed together with synthesis gas into an oxonation unit where catalytic hydroformylation takes place using e.g. hydrocobaltcarbonyl as the active catalyst species. The oxonation unit product passes to a unit for removing catalyst, and then to a hydrogenation unit where it is hydrogenated to form the desired higher alcohol. The product mixture at this stage, comprising the higher alcohol, the high boiling HOF and a low boiling fraction termed the Light Oxo Fraction (LOF), is then passed to a distillation unit where LOF, HOF and desired alcohol product are physically separated.

The LOF passing off overhead is a low value product, typically containing unreacted olefin feed and paraffins. The HOF, as mentioned usually contains dimers such as ethers, esters, aldols and ether-alcohols (e.g. $C_{20}$ compounds for $C_{10}$ production) and trimers such as acetals (e.g. $C_{30}$ compounds for $C_{10}$ alcohol production) and heavier; although substantially alcohol free (apart from the heavy aldols and ether-alcohols), it may contain a minor amount of alcohol which has not been removed in the distillation stage. Again such HOF is conventionally purged from the system at low value. It is desirable, therefore, to develop a more profitable use of HOF which can readily be incorporated into an oxo process system and which serves to increase the yield of more useful products of such a system.

Some such uses have already been proposed. Thus according to U.S. Pat. No. 4,048,233 (Ruhrchemie AG), HOF (termed "thick oil" residue in that document) is converted to synthesis gas ($H_2$/CO mixture) by catalytic splitting at high temperatures using defined proportions of water vapour and carbon dioxide and a catalyst containing from 2 to 25 wt. % nickel, optionally on a carrier such as alumina. The splitting takes place at temperatures of from 600° to 900° C. and pressures up to 30 atmospheres, and the synthesis gas product is recycled to the oxonation unit. Indeed the document teaches that after initial start up the synthesis gas product may constitute the sole supply of said gas to the system. There is no teaching though that useful materials other than synthesis gas may be produced from "thick oil" for recycle to the reaction system.

According to GB Pat. No. 1 411 073 (Kuhlmann) the aldehyde yield of an oxo process for producing aldehydes may be improved by a series of treatments which includes at one point hydroysis of so-called heavy products. In the disclosed technique the crude product from the oxo reactor is first distilled to remove unreacted hydrocarbons, and then distilled to separate the desired aldehyde product. The remaining materials, products of secondary reactions in the oxo reactor, are, without any intermediate hydrogenation (which is considered undesirable and complicated according to page 1 lines 39–50 of the disclosure) then subjected to a further distillation to remove alcohols and formates. Following such removal the alcohol/formate distillate is dehydrogenated and returned to the hydroformylation outlet of the system. The residual heavy products are then catalytically steam hydrolysed at atmospheric pressure, 250°–400° C., and a preferred 1:1 w/w steam ratio to form a mixture of alcohols, aldehydes and residual heavy products, such mixture being recycled to the hydroformylation output after removal of the residual heavy products.

It is noted here that the Kuhlmann method employs no hydrogenation stage; and furthermore that the nature of the secondary reaction products is considerably changed by incorporation of a hydrogenation step into the system. In particular the aldehyde content of the stream is minimised and of course, following hydrogenation there are no formates present in the stream, which formates are necessarily removed prior to hydrolysis in accordance with Kuhlmann.

U.S. Pat. No. 2,757,203 (Hale) also addresses the question of the secondary reactions occuring in the oxo process and in particular identifies that acetals may be formed, thus reducing the aldehyde/alcohol yield. Recognising that acetal formation is acid catalysed, Hale makes use of the equilibrium nature of the reaction by hydrolysing the acetal containing crude product, optionally after hydrogenation, in the presence of aqueous mineral acid at 212°–400° F. whilst simultaneously continuously distilling off the aldehyde. Hale provides no teaching to catalyse the hydrolysis with other than a mineral acid, nor does he propose performing the reaction on the heavy products obtained following removal of alcohol from the crude oxo product.

U.S. Pat. No. 2,779,794 (Catterall) teaches the heat soaking of the crude oxo product in contact with water in order to decompose cobalt catalyst compounds contained therein to an aqueous slurry, but the aim is simply catalyst removal, not any modification of the organic phase. Furthermore, there is no suggestion that catalytic steam hydrolysis might be used in the technique taught.

U.S. Pat. No. 2,905,716 (Buchner et al) teaches the removal of metal and acetals from a crude aldehyde containing oxo product by contacting the stream with water at 150°–200° C. in an elongate, unfilled reactor at elevated pressure, but makes no suggestion to use catalytic techniques nor any indication to recycle the resulting product.

U.S. Pat. No. 3,092,670 (Gwynn et al) teaches the removal of unreacted olefin from the crude oxo product by fractionating the demetalled product in the presence of steam. Subsequently the remaining material, containing polymeric secondary reaction products, is subjected to conventional hydrogenation to yield the desired alcohol product.

U.S. Pat. No. 2,779,796 (Munger) is also concerned with the removal of cobalt from crude oxo product streams and teaches the injection of live steam at 212°–400° F. into the crude product to achieve this objective. During such treatment all the heat required is supplied by the live steam and the crude product is not allowed to come into contact with any fixed heating surface having a temperature greater than the water/product mixture boiling point.

U.S. Pat. No. 2,595,096 (Parker) seeks to improve the alcohol yield of the oxo process by treating the bottoms obtained following oxonation, hydrogenation and removal of, first, unreacted hydrocarbons and then alcohols from the hydrogenated product stream. Such bottoms are said to contain polymerised aldehydes and ketones, high molecular weight ethers and secondary alcohols and polymerised hydrocarbons, principally acetals. The acetal content of the bottoms is hydrolysed with dilute mineral acid, with water (steam) or by other catalytic means to form quantities of alcohols and aldehydes which may themselves be recycled to the hydrogenation stage. Making specific reference to Parker, the process is described at column 5 lines 33–65 with reference to the drawing. Thus the acetal content of the bottoms derived from oxonating a $C_7$ olefin is hydrolysed at 200°–250° F. (91°–121° C.) using 10% aqueous hydrochloric acid solution, although (column 5 line 68-column 6 line 2) there is also disclosure of the possible use of live steam at 300°–400° F. (149°–204° C.). Furthermore, alternatives to dilute mineral acids for the conversion of acetals in the bottoms to aldehydes and alcohols are stated at column 6 lines 23–27 to be other catalytic agents such as alumina, silica and metals or metal oxide of the eighth group of the periodic system. Example I of Parker specifically shows hydrolysis of the bottoms derived from $C_7$ olefin oxonation with an equal volume of water in an autoclave at 350° F. (175° C.), giving an overall alcohol yield increase of 2–3%. Example II takes the same bottoms and, following removal of residual $C_8$ alcohol, hydrolyses them with water alone (steam at 175° C.) and with 10% HCl solution at 220° F. (102° C.) to convert the acetal content to alcohol and aldehyde.

Such relatively mild hydrolysis conditions may be acceptable and useful for improving the alcohol yield of systems which contain bottoms fractions having relatively large proportions of the acetals, but the economic climate of present day higher alcohol production is much worse than in 1949, the date of Parker. There is a greater desideratum to maximise yields of higher alcohol, and heavy bottom products are not readily consigned for fuel use. There is a need therefore for a method which can improve alcohol yield of the oxo process virtually regardless of the nature of the secondary products which may be present in the crude oxo product stream, that is to say even in cases where the acetal content of such crude product streams after hydrogenation is relatively small.

Thus according to the present invention there is provided a process for producing a higher alcohol from an olefinic feedstock by hydroformylating the feedstock with synthesis gas in the presence of a hydroformylation catalyst to form a product mixture containing higher aldehyde, alcohol, unreacted feed and secondary products; removing catalyst therefrom; hydrogenating the substantially catalyst free mixture to convert the higher aldehyde to higher alcohol; distilling the higher alcohol-containing product mixture to separate (i) a lower boiling Light Oxo Fraction (LOF) and (ii) the desired higher alcohol from (iii) a higher boiling Heavy Oxo Fraction (HOF); subjecting the HOF to catalytic steam cracking at a temperature of from 260° to 380° C. using as catalyst an active metal oxide or pseudo-metal oxide, to form HOF residue and a cracked HOF mixture comprising a major proportion of higher alcohol and higher aldehyde, and a minor proportion of olefin and saturated hydrocarbon; and recycling the cracked HOF mixture to the hydroformylation or hydrogenation stage of the process.

The hydroformylation conditions employed to produce the crude product mixture may be those which are well known in the art. For example the hydroformylation reaction may be carried out at a pressure of 150–300 atm, and a temperature of from 125°–175° C. The hydroformylation catalyst used may be for example cobalt in desired active form, preferably in a concentration of from 0.05–3 wt % based on the olefinic feed. Typically the syn gas used might have a $H_2$:CO volume ratio in the range 0.9:1–1.5:1.

The catalysts which may be employed in accordance with the invention (other than the hydroformylation catalyst) are those which promote hydrolysis of the components of the HOF, which generally contains alcohols (assuming not all have been removed in the separation stage), ethers, esters, ether-alcohols and acetals. Thus the catalyst is selected such that the hydrolysis reaction takes place at the rather severe conditions defined to yield a product mixture (the cracked HOF mixture) which is relatively enriched in higher alcohols and aldehydes. The catalysed reactions performed under the specified conditions may be for example acetal hydrolysis, ester hydrolysis, or ether hydrolysis.

It has been found that the desired reactions take place in the presence of metal or pseudo-metal oxides in the active state, such as silica, alumina or titanium dioxide, or mixed silica/alumina. It is particularly preferred to employ alumina as the hydrolysis catalyst. Such catalysts, under the temperature specified, at least partially convert the HOF components to alcohols and aldehydes.

The temperature at which the HOF steam cracking step is performed is most preferably in the relatively high range of 290° to 360° C., and preferably at pressures of from 100 to 1000 kPa (1–10 bar), more preferably 1–3 atm abs. It is preferred that the hydrolysis of the HOF is performed with the weight ratio of steam and HOF in the range 0.1:1 to 2:1, more preferably 0.2:1 to 1.2:1. In general, the higher the steam ratio, the better is the selectivity to aldehyde/alcohol rich cracked HOF mixture, but for economic reasons the optimum range has been found to be from 0.15:1 to 0.5:1.

The use of an active metal or pseudo-metal oxide hydrolysis catalyst in accordance with the invention, particularly alumina, at 260°–380° C. yields a cracked HOF mixture which is useful to the oxo-process operator for improving alcohol yield since it contains more aldehyde/alcohol than olefin. In particular it has been found that steam cracking of HOF using an alumina catalyst at 260°–380° C. yields HOF residue and a cracked HOF mixture which may comprise up to 90% alcohol/aldehyde and some 10% olefinic hydrocarbon based on the total alcohol/aldehyde/olefin content of the mixture. In general, for a particular catalyst, increasing steam cracking temperature has been found to give increased overall conversion of the HOF but reduced selectivity to the alcohol/aldehyde component.

A reduced selectivity to alcohol/aldehyde results, on recycle of the material to the hydrogenation stage of the process, in an increased make of LOF, and it will be recognised that the HOF cracking temperature range specified for the process of the invention is intended to reflect those temperatures which yield a cracked HOF mixture having components which yield an economic benefit from increased yield of desired higher alcohol. Too low a temperature will not give conversions which make the capital expenditure associated with HOF cracking worthwhile; whereas too high a temperature will increase olefin/paraffin make, hence LOF make if recycle is to the hydrogenation stage, and this too will be detrimental to the economics of the process.

The steam cracking of the HOF in accordance with the invention yields as well as the cracked HOF mixture, a HOF residue which is typically oxygenated dimers and trimers ($C_{20}$ to $C_{30}+$ materials for a $C_{10}$ alcohol). Unless the cracked HOF mixture is automatically separated from the HOF residue during the steam cracking step (by virtue of the particular cracking technique employed), the HOF residue should be removed in a subsequent stage (preferably steam or flash distillation) prior to recycle of the cracked HOF mixture. It is particularly preferred that any water remaining in the cracked HOF mixture from the hydrolysis stage should be removed before recycling the mixtures since the presence of water in the crude oxo product delivered to the hydrogenation stage could damage the hydrogenation catalyst employed.

Preferably the cracked HOF mixture is recycled to the hydrogenation stage of the process, although it is of course possible to introduce the mixture at the hydroformylation stage so as to provide some upgrade of its admittedly low olefin content to higher aldehyde and ultimately higher alcohol. Economic considerations would usually require recycle to the hydrogenation stage, since recycle to the hydroformylation stage might result, by virtue of the major proportion of alcohol/aldehyde in the mixture, in an increased production of undesirable by-products, and also an unnecessary increase in operating costs. However recycle to the hydroformylation stage may be elected if for some reason the cracking conditions have resulted in a cracked HOF mixture containing a proportion of olefin/paraffin approaching that of alcohol/aldehyde. Thus there are two recycle options for the cracked HOF mixture produced in the HOF steam cracking stage and containing higher aldehyde, higher alcohol and a minor proportion of olefinic hydrocarbon and saturated hydrocarbons. In the first option, recycle is to the hydrogenation stage of the oxo process. Here the higher alcohol passes through unconverted, the higher aldehyde is converted to higher alcohol, and the olefinic hydrocarbon is either reduced or, as with saturated hydrocarbons, passes through unchanged: at the subsequent distillation stage the higher alcohol is removed as the desired product of the overall process and the olefinic and saturated hydrocarbons are removed as LOF.

Alternatively the cracked HOF mixture is recycled to the hydroformylation stage: here aldehyde and alcohol either undergo reactions to generate undesirable by-products, or pass through unconverted to the hydrogenation stage where the aldehyde is reduced to the desired higher alcohol; olefinic hydrocarbons are oxonated and upgraded to the higher aldehyde/alcohol, which higher aldehyde is reduced to desired higher alcohol at the hydrogenation stage; and saturated hydrocarbons pass through the entire system unreacted, being substantially removed (together with unreacted olefins) as LOF at the distillation stage. The recycle route selected by the operator will depend on the economics of the particular plant operation, and of course the feed available and desired end product.

Repeated performance of the process according to the invention has shown that the HOF typically has a composition comprising 0–5 wt. % alcohols, 15–25 wt. % ethers, 45–65 wt % ether-alcohols 2–10 wt % esters, and 5–25 wt % acetals, with possibly extremely minor amounts of other materials, e.g. up to 2 wt % heavier depending on feedstock and selected process conditions. Depending on the feed to the oxo reactor, such HOF is typically the material boiling in the range 200°–450° C. at atmospheric pressure. The HOF residue produced after cracking typically comprises 0–10 wt % alcohol/aldehyde (for example up to 7 wt % total of aldehyde), 45–75 wt % ethers, 20–35 wt % ether-alcohols, 0–7 wt % esters, 1–6 wt % acetals and for example up to 1 wt % heavier. Again depending on the oxo-feed, such HOF residue typically boils at temperatures above 200°–220° C. at atmospheric pressure, although as will be understood, the attribution of a specific boiling temperature to a complex mixture of components is not easy, depending amongst other things on whether distillation is on a continuous or batch basis, the length of the distillation column and the point or phase in the column at which temperature is measured. The cracked HOF mixture will typically comprise 60–85 wt % alcohol/aldehyde, 0–20 wt % olefin/saturated hydrocarbon and 0–20 wt % HOF residue; the amounts of these components will depend on the carbon numbers of the feedstock and the degree of separation required by the operator. The boundary between the cracked HOF mixture and the HOF residue depends to an extent on the wishes of the process operator and the economics of his particular oxo-process. It is generally the case that the HOF residue comprises substantially the dimer and trimer and even heavier components of the organic phase produced by cracking the HOF under the specified conditions. Preferably the mixture which is recycled to the process (ideally to hydrogenation) is the one which is substantially the monomer components of the cracked HOF organic phase, that is those compounds containing one more carbon atom in their molecules than the carbon number of the feedstock to the overall process. Preferably the cracked HOF mixture will contain no more than about 20 wt % of dimers and above, whilst the residue preferably contains less than 10 wt % of monomeric components.

Since the cracking reaction shows a progressively increasing conversion with temperature, but selectivity to alcohol/aldehyde reaches a maximum then falls off with increasing temperature, there is a maximum in alcohol/aldehyde yield to which it is desirable to progress by control of temperature. Bearing this in mind, it is preferred that the mixture as recycled should contain alcohol/aldehyde in amounts which correspond to greater than about 30 or 40 wt % of the organic material obtained following cracking of the HOF. It is particularly preferred that the amount should correspond to greater than about 50 wt % since this helps to maximise the overall process yield of higher alcohol. With regard to the cracked HOF mixture as recycled in accordance with the invention, this should contain a major proportion of alcohol/aldehyde components based on the total of alcohol/aldehyde components plus olefin/paraffin components. On this basis, the mixture preferably contains from 70-98 wt %, more preferably 80-95 wt % and especially 85-92 wt % of the alcohol/aldehyde component.

The process according to the invention is particularly suitable for use with branched olefin feedstocks preferably those with carbon numbers $C_6$ to $C_{12}$, more preferably $C_8$ to $C_{10}$, and results in improved yields of branched higher alcohol, and also in by-products having higher value. In particular, the HOF residue which is the product of the process has been found to be a surprisingly useful material. The HOF residue contains substantially dimeric, trimeric and heavier compounds based on the original feedstock, and preferably contains a minor amount eg less than 10 wt % of monomeric compounds derived from the feedstock.

The following Examples illustrate the invention.

EXAMPLE 1

(1) Hydroformylation stage

Hydroformylation was performed using a feed comprising (i) syn gas containing hydrogen and carbon monoxide in a molar ratio of 1.16:1 and (ii) a commercially available stream of branched nonenes including also about 2 wt % octenes and about 8 wt % decenes. The olefin feed was delivered at a rate of 1.5 l/hr (1115 g/hr), and the syn gas at a rate of 640 standard l/hr, into three 1.0 liter capacity oxonation reactors arranged in series, and the reaction was carried out at a pressure of 300 atm and a temperature of 175° C., using a cobalt catalyst at 0.3 wt % based on the feed.

(2) Decobalting stage

The crude oxo product containing higher aldehyde, resulting from stage (1) was decobalted to less than 10 ppm cobalt in conventional manner by neutralizing the cobalt hydrocarbonyl with sodium hydroxide and washing with water.

(3) Hydrogenation stage

The product of stage (2) was fed to a conventional hydrogenation train where, using Cu/Cr and Ni catalysts, a hydrogen pressure of 50 bars and a temperature of 120°-170° C. the product containing higher aldehydes, formates and acetals was converted to a hydrogenation product mixture containing the desired higher alcohol.

(4) Separation stage

The mixture of stage (3) was then distilled under vacuum to produce three fractions, a light oxo fraction (LOF), a heavy oxo fraction (HOF) and a higher alcohol fraction (HA) as shown in Table 1.

TABLE 1

| Fraction | Amount | Alcohol content | Boiling Range |
|---|---|---|---|
| LOF | 150 g/hr | $\leq$0.5 wt % | 125-187° C. |
| HA | 1010 g/hr | | 187-217° C. |
| HOF | 223 g/hr | $\leq$3 wt % | >217° C. |

The higher alcohol yield (chiefly $C_{10}$, with minor amounts of $C_9$ and $C_{11}$) was 90.58 g per 100 g of feed olefin.

By analysis the HOF was shown to comprise approximately:

2 wt % $C_9$–$C_{11}$ alcohols
85 wt % $C_{18}$–$C_{22}$ esters, ethers and ether-alcohols
12 wt % $C_{27}$–$C_{33}$ acetals
1 wt % Heavies

(5) HOF cracking stage

The HOF product separated in stage (4) was introduced in upflow manner and in admixture with half its weight of steam into a steam cracking reactor. The reactor was packed with an active alumina catalyst ALCOA H151 and operated at 318° C., and a pressure of 1.2 atm. The flow of HOF/steam through the reactor was such as to correspond to a space velocity of 0.5 v/v/hr expressed as volume of HOF per volume of catalyst per hour. After cracking, the cracked product was subjected to flashing at 200° C., to produce an overhead stream comprising cracked HOF mixture and water (steam), and a bottoms stream of HOF residue. After condensation of the overheads, the water phase was separated from the cracked HOF mixture. The HOF residue comprised a major proportion of oxygenated compounds of carbon number $C_{18}$–$C_{30}$ (predominantly $C_{18}$–$C_{22}$) with some even heavier products, and a minor proportion of alcohol/aldehyde/olefin components. The cracked HOF mixture comprised a small proportion of HOF residue, a smaller proportion of an olefin fraction, generally $C_8$–$C_{11}$ olefins with predominantly $C_{10}$ olefin and a very low level of saturated hydrocarbon, and a major proportion of an alcohol/aldehyde mixed fraction with carbon numbers $C_9$–$C_{11}$, predominantly $C_{10}$.

The compositions of cracked HOF mixture and HOF residue are shown in Table 2.

TABLE 2

| | Composition (wt %) |
|---|---|
| Cracked HOF mixture (169 g/hr) | |
| olefin | 7.0 |
| alcohol/aldehyde (1) | 75.5 |
| HOF residue | 17.5 |
| HOF residue (54 g/hr) | |
| alcohol/aldehyde | 6.2 |
| HOF residue | 93.8 |

(1) Weight ratio of alcohol:aldehyde in cracked HOF mixture was 3.1:1.

On the basis of the above it may be calculated that the cracked HOF mixture produced in the cracking stage represents a potential alcohol increase (based on the amount of HOF and taking into account the original 2 wt % alcohol content of the HOF) of 55.2 percentage points. That is, the original 223 g/hr HOF containing 4.46 g/hr (2 wt %) alcohol has been converted to 169 g/hr of cracked HOF mixture containing 127.59 g/hr (75.5 wt %) alcohol/aldehyde; this amount corresponds to 57.2 wt % of the original 223 g/hr stream, or 123.13 g/hr increase in the amount of alcohol/aldehyde available to the operator (not counting the amount of alcohol/aldehyde contained in the HOF residue component). A similar calculation shows that the olefin content of the HOF has been increased by 5.3 percentage points, being an increase of 11.83 g/hr of olefin available to the operator.

(6) Recycle stage

The cracked HOF mixture of stage (5) was recycled to hydrogenation stage (3) of the process by incorporation at a rate of 169 g/hr into a stream of 1383 g/hr of decobalted oxo product obtained following stage (2). Stages (3) and (4) were thus performed on the recycle blend to yield the three fractions as shown in Table 3.

TABLE 3

| Fraction | Amount | Alcohol content | Boiling Ranges |
|---|---|---|---|
| LOF | 180 g/hr | <0.5 wt % | 130–190° C. |
| HA | 1116 g/hr | | 190–219° C. |
| HOF | 256 g/hr | <3 wt % | >219° C. |

The HA yield was thus 100.1 g per 100 g of olefin feed, compared with 90.58 g for the process without HOF cracking and recycle, an improvement of about 12% on the overall process.

EXAMPLE 2

(1) Hydroformylation stage

Hydroformylation was performed in the same apparatus as Example 1 under conditions of 165° C., 300 atm and using cobalt catalyst at 0.15 wt % based on the feed. However, the feed in this case was 1.5 l/hr (1095 g/hr) of a commercial branched octene feed containing in addition to $C_8$ olefin, about 1% of $C_7$ olefins and about 10% of $C_9$ olefins. The syn gas was employed at a rate of 750 standard litres/hr, and contained hydrogen and carbon monoxide in a ratio of 1.18:1.

Stages (2) and (3) were performed as in Example 1, with the hydrogenated product of stage (3) being separated in stage (4) by distillation into the three fractions as shown in Table 4. The HOF was selected as the fraction boiling at 206° C. and above.

TABLE 4

| Fraction | Amount | Alcohol content | Boiling Ranges |
|---|---|---|---|
| LOF | 150 g/hr | ≦0.5 wt % | 113–184° C. |
| HA | 1013 g/hr | | 184–206° C. |
| HOF | 219 g/hr | ≦3 wt % | >206° C. |

This yield of higher alcohol corresponds to an amount of 92.5 g per 100 g of feed olefin. By analysis the HOF was shown to have the composition:
1 wt % $C_8$–$C_{10}$ alcohols
87 wt % $C_{16}$–$C_{20}$ ethers, esters and ether-alcohols
11 wt % $C_{24}$–$C_{30}$ acetals
1% Heavies (5) HOF cracking The HOF from stage (4) was subjected to catalytic steam cracking in a reactor packed with ALCOA H 151, at 310° C., a pressure of 1.1 atm and a space velocity of HOF equal to 0.47 v/v/hr. The amount of steam used was 25% of the weight of HOF. Two cracked product streams were obtained, as in Table 5, following flash at 196° C. and removal of water, the cracked HOF mixture being the flash vapour phase and the HOF residue being the flash liquid phase.

TABLE 5

| | Composition (wt %) |
|---|---|
| Cracked HOF mixture (173 g/hr) | |
| olefin | 10 |
| alcohol/aldehyde (1) | 69.2 |
| HOF residue | 20.8 |
| HOF residue (46 g/hr) | |
| alcohol/aldehyde | 7 |
| HOF residue | 93 |

(1) The alcohol:aldehyde weight ratio in the cracked HOF mixture was 2.8:1

Calculations from the above values show that the 219 g/hr HOF stream containing 1 wt % (2.19 g/hr) alcohol has been converted to a 173 g/hr cracked HOF mixture stream containing 69.2 wt % (119.71 g/hr) of alcohol/aldehyde, corresponding to an increase of 117.52 g/hr of alcohol/aldehyde (53.6 percentage points increase based on the original HOF stream). The olefin increase on the same basis is 17.3 g/hr, or 7.9 percentage points based on the HOF stream.

The HOF residue was found to comprise mainly $C_{10}$–$C_{27}$ oxygenated compounds, predominantly $C_{16}$–$C_{20}$ materials, with a few other minor components including some aldehyde/alcohol and traces of olefin. The olefin fraction of the cracked HOF mixture was a mixture of $C_7$–$C_{10}$ olefins, predominantly $C_9$'s together with small amounts of saturated hydrocarbons. The alcohol/aldehyde fraction contained a $C_8$–$C_{10}$ range, with a major amount of $C_9$ alcohols/aldehydes.

(6) Recycle

Recycle to the hydrogenation stage was carried out as described in Example 1 by delivering 173 g/hr of the cracked HOF mixture together with 1382 g/hr of oxo product from decobalting stage (2), into the hydrogenation and separation stages (3) and (4) described above. The three fractions resulting from stage (4) are shown in Table 6.

TABLE 6

| Fraction | Amount | Alcohol content | Boiling Ranges |
|---|---|---|---|
| LOF | 169 g/hr | ≦0.5 wt % | 115–185° C. |
| HA | 1133 g/hr | | 185–205° C. |
| HOF | 253 g/hr | ≦3 wt % | >205° C. |

This HA yield following HOF cracking and recycle corresponds to 103.5 g alcohol per 100 g olefin feed, compared with 92.5 g/100 g without cracking and recycle, an improvement of about 12% on the process overall.

EXAMPLE 3

The HOF product (223 g/hr) produced in accordance with stages (1)–(4) of Example 1 was subjected to HOF cracking in a manner identical with stage (5) of Example 1 except that the cracking temperature employed was 378° C. After cracking, the total reactor effluent was condensed and the water separated from the organic phase. The total (223 g/hr) organic phase, that is the unseparated cracked HOF mixture and HOF residue, was found to have the following composition:
28.8 wt % $C_9$–$C_{11}$ olefins/paraffins
39.0 wt % $C_9$–$C_{11}$ alcohols/aldehydes
31.6 wt % $C_{18}$–$C_{22}$ esters, ethers and ether-alcohols
0.4 wt % $C_{27}$–$C_{33}$ acetals
0.2 wt % heavies The total organic phase was not separated into cracked HOF mixture and HOF residue (ie dimers and above) and hence there was no recycle to the hydrogenation unit; thus this example does not strictly exemplify the present invention. However it does serve to demonstrate that at the upper end of the HOF cracking temperature range there is less useful selectivity to the alcohol/aldehyde components, and a corresponding increase in the amount of olefins produced. The analytical data presented above may be theoretically split into a notional "cracked HOF mixture" (the $C_9$–$C_{11}$ compounds) and a notional "HOF residue" (the $C_{18}$–$C_{33}$ dimers, trimers and even heavier compounds). On the basis of this theoretical split, it is seen that the cracked HOF mixture, being 67.8 wt % of the total organic phase, would comprise 57.52% alcohol/aldehyde and 42.48% olefin/paraffin. The advantages of recycling such a mixture through the overall process (to hydroformylation or hydrogenation stages) are not as great as with more alcohol/aldehyde rich mixtures (see Example 1 for example, where the recycled mixture contains alcohol/aldehyde: olefin/paraffin in a weight ratio of about 10:1). Thus although the cracking makes more alcohol available to the operation (in fact 37.0 percentage points or 82.4 g/hr more, allowing for the original 2% alcohol content of the HOF), and recycle would place the process within the scope of the present invention, the economic incentive for such a technique diminishes as cracking temperature increases and the reaction is seen to become more selective to olefins. With such a mixture, recycle to hydroformylation for upgrading of the olefin content is preferred, but it is generally more preferred to adapt the cracking conditions so as to improve alcohol/aldehyde make and permit advantageous recycle to the hydrogenation stage.

EXAMPLE 4

Example 3 was repeated but with a cracking temperature of 263° C. By analysis the total (223 g/hr) organic phase obtained was shown to comprise:
1.1 wt % $C_9$–$C_{11}$ olefins/paraffins
37.9 wt % $C_9$–$C_{11}$ alcohols/aldehydes
53.4 wt % $C_{18}$–$C_{22}$ esters, ethers, ether-alcohols
7.1 wt % $C_{27}$–$C_{33}$ acetals
0.5 wt % heavies Again, the total organic phase was not separated into cracked HOF mixture (monomers) and HOF residue (dimers and above), but the results may be analysed to show that by operating at the lower end of the HOF cracking temperature range, although there is good selectivity to alcohol/aldehyde, there is poor conversion. Thus the notional "cracked HOF mixture" (monomers) constitutes some 97 wt % of the desirable alcohol/aldehyde component, but represents only 39.0 wt % of the total organic phase, and so is seen to be of reduced economic attraction to the operator.

EXAMPLE 5 (Comparison)

The HOF produced by performing the hydroformylation, decobalting, hydrogenation and separation stages of Example 1 was further treated to remove substantially all the alcohol, yielding a HOF having the composition:
0 wt % $C_9$–$C_{11}$ alcohol
88.5 wt % $C_{18}$–$C_{22}$ esters, ethers and ether-alcohols
10.6 wt % $C_{27}$–$C_{33}$ acetals
0.9 wt % Heavies The HOF cracking reactor of Example 1 was filled with distillation column packing (inert stainless steel balls) to provide appropriate surface area, and the HOF cracking procedure of Example 1 was performed on the above composition, but without the presence of the alumina catalyst and at a temperature of 358° C. and a pressure of 1.15 atm abs. The resultant mixture, after water removal, was analysed and found to have the following composition:
0.3 wt % olefins
5.0 wt % alcohols, aldehydes
84.1 wt % esters, ethers, ether-alcohols
9.4 wt % acetals
0.6 wt % heavies Thus it is seen that uncatalysed cracking of the HOF under conditions otherwise substantially the same as those used in accordance with the invention gave only 5 wt % of alcohol/aldehyde in the final product. This is to be compared with Example 1 where the alcohol/aldehyde content of the two streams (cracked HOF mixture and HOF residue) derived by catalytic steam cracking of the starting HOF amounted to 58.7 wt %.

I claim:

1. A process for producing higher alcohols from an olefinic feedstock comprising olefins containing from 6 to 12 carbon atoms which comprise: (a) hydroformylating said olefinic feedstock with synthesis gas in the presence of a cobalt-containing hydroformylation catalyst to form a hydroformylation product mixture containing higher aldehydes and higher alcohols having a carbon number which is one carbon atom greater than said olefinic feedstock, unreacted olefinic feedstock and secondary reactions products; (b) treating said hydroformylation product mixture to remove said hydroformylation catalyst therefrom and to form a decobalted hydroformylation product mixture; (c) hydrogenating said decobalted hydroformylation product mixture to convert said higher aldehydes to additional amounts of said higher alcohols; (d) distilling the higher alcohol-containing hydrogenation product mixture formed in step (c) to separate (i) a lower boiling light oxo fraction and (ii) said higher alcohols from (iii) a higher boiling heavy oxo fraction; (e) subjecting the heavy oxo fraction to catalytic steam cracking at a temperature of from 260° to 380° C. in the presence of a cracking catalyst selected from the group consisting of active metal oxides and pseudo-metal oxides, to form a cracked heavy oxo fraction mixture comprising a major proportion of higher alcohol and higher aldehyde, and a minor proportion of olefin, saturated hydrocarbon and uncracked heavy oxo fraction residue; and (f) recycling said cracked heavy oxo fraction mixture to the hydroformylation or hydrogenation stage of the process.

2. A process according to claim 1 wherein said cracking catalyst, comprises alumina.

3. A process according to claim 1 wherein said catalytic steam cracking of said heavy oxo fraction is performed using steam and heavy oxo fraction at a weight ratio in the range 0.1:1–2:1.

4. A process according to claim 3, wherein said catalytic steam cracking said heavy oxo fraction is performed using steam and heavy oxo fraction at a weight ratio in the range 0.15:1–0.5:1.

5. A process according to claim 1 wherein said catalytic steam cracking of said heavy oxo fraction is performed at a total pressure of from 1–10 atm abs.

6. A process according to claim 5, wherein said pressure is from 1-3 atm abs.

7. A process according to claim 1 wherein said catalytic steam cracking is performed at a temperature of from 290°-360° C.

8. A process according to claim 1 wherein said cracking heavy oxo fraction mixture is recycled to the hydrogenation stage.

9. Heavy oxo fraction mixture comprising 0-10 wt % alcohol/aldehyde, 45-75 wt % ethers, 20-35 wt % ether-alcohols, 1-6 wt % acetals and 0-7 wt % esters wen produced by the process according to claim 1.

10. Heavy oxo fraction residue comprising substantially a mixture of dimeric, trimeric and heavier compounds produced by the process according to claim 1.

11. Heavy oxo fraction residue according to claim 10 which comprises dimeric compounds of carbon number $C_{14}-C_{26}$ and trimeric compounds of carbon number $C_{21}-C_{39}$.

12. Heavy oxo function residue according to claim 10 which contains no more than 10 wt % of monomeric compounds.

13. A process according to claim 1 wherein said hydroformylation step (a) performed at a temperature of from 125° to 175° C. and at a pressure of from 150 to 300 atm., and wherein said catalytic steam cracking step (e) is performed at a pressure of from 1 to 10 atm. abs. and employing steam and said heavy oxo fraction in a weight ratio of from 0.1:1 to 2:1 and employing alumina as said cracking catalyst, to form a cracked heavy oxo fraction mixture which is treated to separate therefrom a heavy oxo fraction residue comprising dimeric and heavier components based on said higher alcohol carbon number and no more than 10 wt. % of monomeric components, and a separated cracked heavy oxo fraction mixture comprising monomeric components based on said higher alcohol carbon number and no more than 20 wt. % of dimeric and heavier components and containing a major proportion of higher alcohol and higher aldehyde, and a minor proportion of olefin and saturated hydrocarbon; and recycling the separated cracked heavy oxo fraction mixture to the hydrogenation stage of the process.

14. Heavy oxo fraction comprising ethers, ether-alcohols and acetals when produced by the process according to claim 13.

* * * * *